United States Patent [19]
Katoh et al.

[11] Patent Number: 5,935,108
[45] Date of Patent: Aug. 10, 1999

[54] RECANALIZATION APPARATUS AND DEVICES FOR USE THEREIN AND METHOD

[75] Inventors: Osamu Katoh, Kyoto, Japan; Mir A. Imran, Los Altos Hills, Calif.

[73] Assignee: Reflow, Inc., Menlo Park, Calif.

[21] Appl. No.: 08/970,911

[22] Filed: Nov. 14, 1997

[51] Int. Cl.⁶ ................................................ A61M 29/00
[52] U.S. Cl. ........................ 604/164; 604/280; 604/49; 606/194
[58] Field of Search ..................... 604/164, 165, 604/171, 280–284, 49, 19, 28; 606/191–194

[56] References Cited

U.S. PATENT DOCUMENTS

| | | | |
|---|---|---|---|
| 4,306,562 | 12/1981 | Osborne ................................. | 604/280 |
| 5,190,528 | 3/1993 | Fonger et al. ....................... | 604/164 X |
| 5,527,292 | 6/1996 | Adams et al. ........................... | 604/171 |
| 5,716,410 | 2/1998 | Wang et al. ............................ | 604/281 |
| 5,720,735 | 2/1998 | Dorros ................................. | 606/194 X |
| 5,776,114 | 7/1998 | Frantzen et al. ........................ | 604/281 |
| 5,810,867 | 9/1998 | Zarbatany et al. ................... | 606/194 X |
| 5,827,201 | 10/1998 | Samson et al. ...................... | 604/281 X |

*Primary Examiner*—John D. Yasko
*Attorney, Agent, or Firm*—Flehr Hohbach Test Albritton & Herbert LLP

[57] ABSTRACT

Recanalization apparatus for crossing a stenosis forming a total occlusion in a lumen in a vessel formed by a vessel wall. The stenosis has a fibrous cap comprising a guiding sheath comprised of a flexible elongate tubular member having proximal and distal extremities. A lumen extends from the proximal extremity to the distal extremity. A hemostasis valve is mounted on the proximal extremity of the flexible elongate tubular member. A needle cannula is slidably mounted in the lumen of the guiding sheath and has proximal and distal extremities and has a lumen extending from the proximal extremity to the distal extremity. A sharpened tip is mounted on the distal extremity. The needle cannula has a length so that its proximal extremity extends beyond the proximal extremity of the guiding sheath when the sharpened tip is deployed beyond the distal extremity of the guiding sheath.

19 Claims, 4 Drawing Sheets

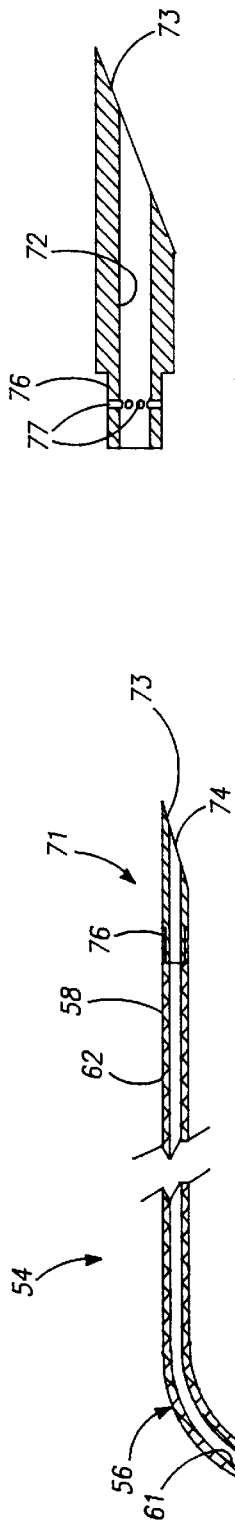
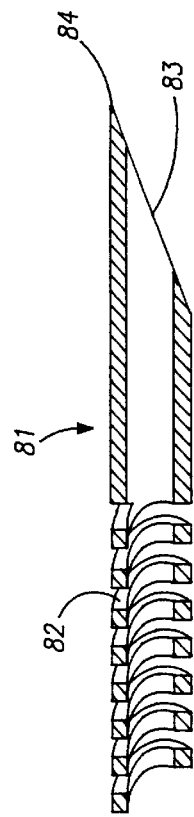
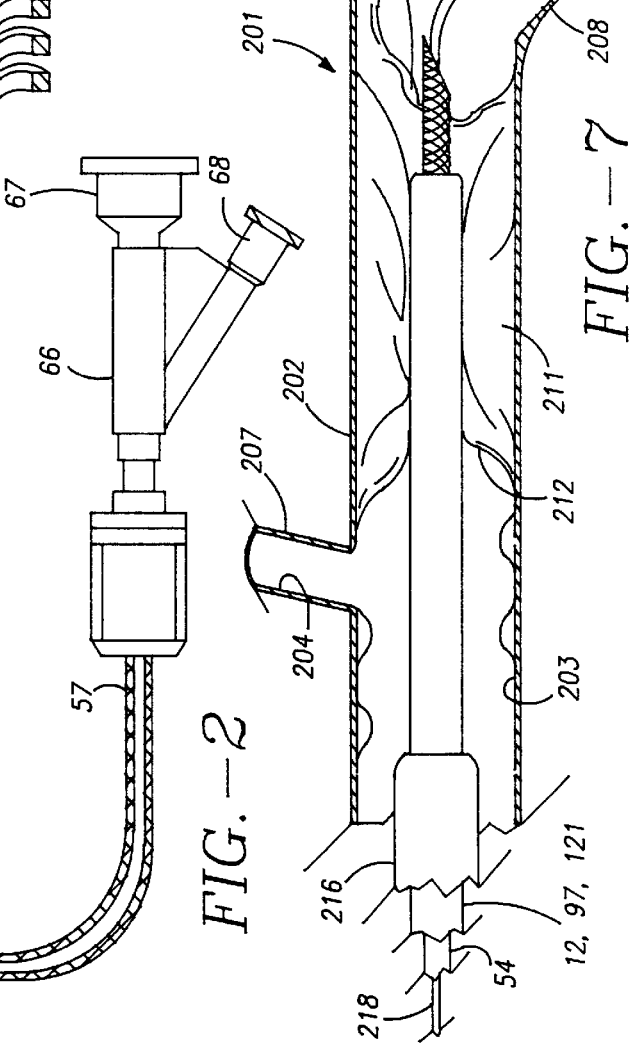

RECANALIZATION APPARATUS AND DEVICES FOR USE THEREIN AND METHOD

This invention relates to a recanalization apparatus and devices for use therein and method.

Chronic total occlusions are quite common in diseased coronary vessels and typically occur where plaque is formed in the vessel, gradually reducing the size of the lumen in the vessel until it becomes quite small and results in thrombus formation resulting in a a stenosis forming a total occlusion. As the total occlusion becomes chronic, the stenosis or lesion generally has a tendency to continue to grow with fibrous end caps being formed at the proximal and distal ends of the occlusion. These fibrous end caps tend to be fairly tough but do have varying degrees of toughness. In attempting to treat such chronic occlusions, there is a need to have guide wires which can extend through the stenoses forming the chronic occlusions so that various types of treatments can be performed. Heretofore attempts to place guide wires across such stenoses or lesions have resulted in the guide wires following fissures in the plaque and creating false lumens or with the guide wire being directed in such a manner so as to perforate the wall of the vessel. In attempting to perform such a guide wire crossing, it often has been necessary to exchange the guide wire for a stiffer wire, all of which is time consuming with often undesirable results. Therefore there is a need for a new and improved recanalization apparatus and devices for use therein and method which overcomes these difficulties.

In general, it is an object of the present invention to provide a recanalization apparatus and a devices for use therein and method which makes it possible to treat totally occluded and substantially occluded vessels.

Another object of the invention is to provide recanalization devices and method which are capable of penetrating particularly difficult chronic totally occluded vessels including those which have fibrous caps.

Another object of the invention is to provide a recanalization apparatus and a device and method in which the device can be positioned so that its distal extremity is in engagement with the fibrous end cap of a stenosis or lesion forming the total occlusion and so that the longitudinal axis extends in a direction which is substantially perpendicular to the fibrous end cap.

Another object of the invention is to provide a recanalization apparatus and device and method which makes possible precise positioning of the distal extremity of the guiding sheath.

Additional objects and features of the invention will appear from the following description in which the preferred embodiments are set forth in detail in conjunction with the accompanying drawings.

FIG. 2 is a side-elevational view of a needle cannula partially in section of the needle cannula utilized in the guiding sheath shown in FIG. 1.

FIG. 3 is a sectional view of another embodiment of a tip for use in the needle cannula shown in FIG. 2.

FIG. 4 is another side elevational view in section of another embodiment of a tip for use in the needle cannula shown in FIG. 2.

FIG. 7 is a cartoon showing the recanalization apparatus being used to perform in a procedure in accordance with the present method.

In general, the recanalization apparatus of the present invention is for use in crossing a stenosis forming a total occlusion in a vessel formed by a vessel wall with the total occlusion having a fibrous end cap. The apparatus is comprised of a guiding sheath comprised of a flexible elongate tubular member having proximal and distal extremities and having a lumen extending from the proximal extremity to the distal extremity. Hemostatic valve means is mounted on the proximal extremity of the flexible elongate tubular member. A needle cannula is slidably mounted in the lumen of the guiding sheath. The needle cannula has proximal and distal extremities and has a lumen extending from the proximal extremity to the distal extremity. A sharpened tip is provided on the distal extremity of the needle cannula. The needle cannula has a length so that its proximal extremity extends beyond the proximal extremity of the guiding sheath when the sharpened tip is deployed beyond the distal extremity of the guiding sheath.

Figure 1:
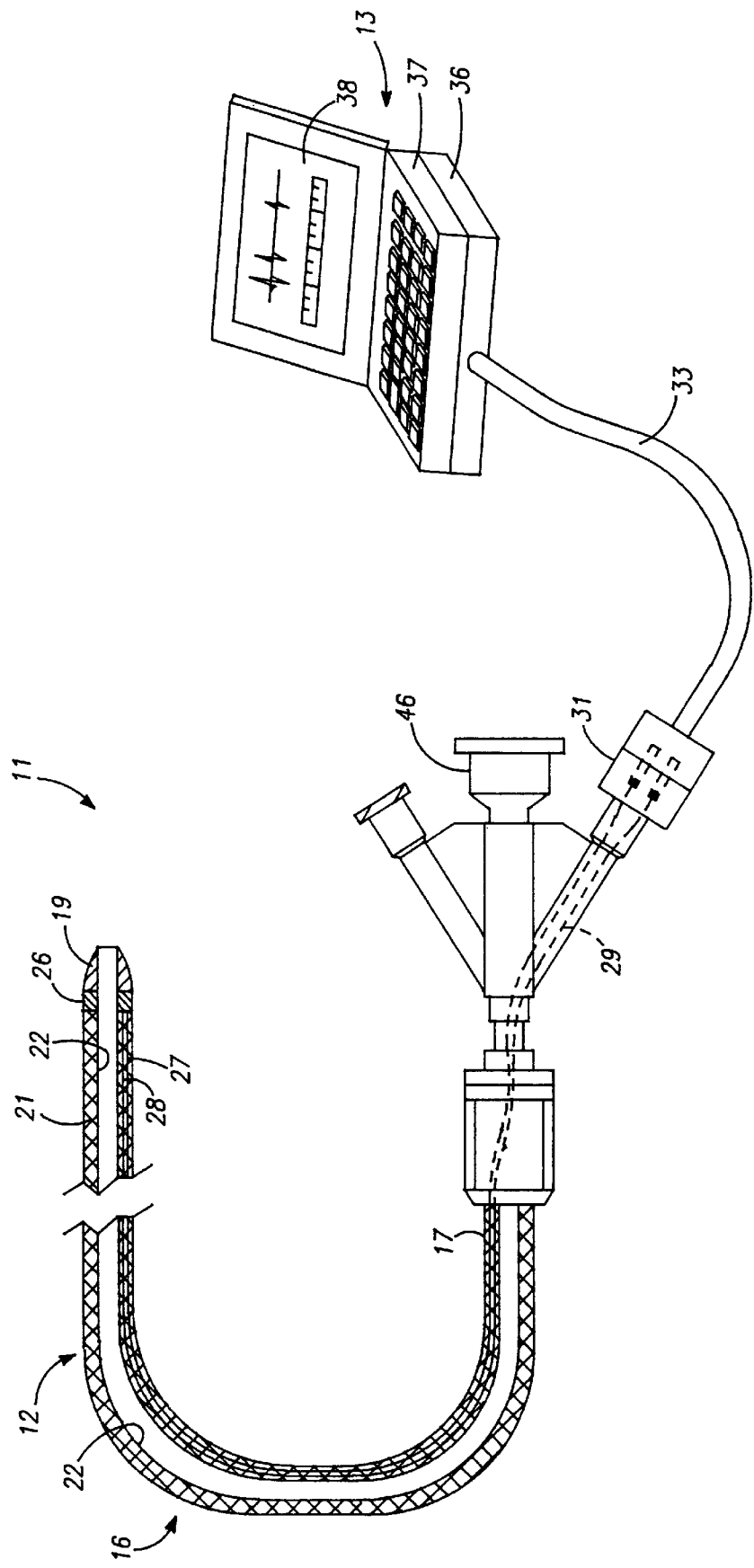
FIG. 1 is a view of a portion of the recanalization apparatus incorporating the present invention and showing a side-elevational view partially in section of the guiding sheath used therein.

More in particular as shown in FIG. 1, the recanalization apparatus 11 consists of a guiding sheath or guiding catheter 12, an ultrasonic power supply 13 and a needle cannula 14. The guiding sheath 12 consists of a flexible elongate tubular member 16 having proximal and distal extremities 17 and 18. The tubular member 16 can be formed of a suitable material such as a plastic. In order to provide kink resistance and torquability, the tubular member 16 can incorporate a braid or a coil 21 therein which can extend from the proximal extremity 17 to the distal extremity 18. However, if desired, the braid or coil can be provided only in a portion of the tubular member 16 as for example only in the distal extremity. The tubular member 16 can have a suitable length as for example ranging from 120–150 cm. It is provided with a lumen 22 extending the length thereof of a suitable size as for example an inside diameter ranging from 0.012" to 0.020" with the outside diameter ranging from 0.020" to 0.024". A ring-type or annular ultrasonic transducer 26 is carried on the distal extremity 18 just proximal as for example 2 mm of a soft tip 19 and is formed of a suitable material such as lead zirconate titanate. The transducer 26 serves as sensing means and propagates energy in a transverse mode by vibrating along the axis of the transducer 26 to create an ultrasonic wave propagating forwardly from the distal extremity 18 of the guiding sheath 12. If desired, the transducer can also provide sidewise propagating waves. Insulated electrical conductors 27 and 28 are connected to the transducer 26 and are embedded in the wall forming the tubular member 16 and extend to the proximal extremity 17 of the tubular member 16. Alternatively to a twisted pair of conductors 27 and 28 formed of two of the wires of the braid 21 can be utilized for supplying electrical energy to the ultrasonic transducer 26 and also for picking up electrical signals created by the reflected ultrasonic waves picked up by the transducer 26. The conductors 27 and 28 extend into a cable 29 which is provided with a connector 31 which is mated with another connector 32. The connector 32 is connected by a cable 33 to an ultrasonic power supply and imaging system 36 which underlies a notebook computer 37 having a hinged cover display screen 38.

A conventional hemostasis valve 46 is mounted on the proximal extremity 17 of the flexible elongate member 16. The hemostasis valve is mounted on a hub 47 which carries a saline flush port 48.

The ultrasonic power supply 36 generates very narrow high energy pulses that are supplied to the transducer 26 to cause it to vibrate at a particular frequency, causing the generation of ultrasonic waves that are propagated forwardly through the blood in the vessel with the reflected ultrasonic waves coming back and being picked up by the transducer and converted to electrical signals which are supplied to the conductors 27 and 28. Typically a frequency of 5 to 40 MHZ can be utilized. The transducer 26 is operating in the A mode and is used for ranging to tell the distance from the interior wall forming the lumen of the vessel to the transducer 26. When the ultrasonic waves are traveling through a lumen in which there is blood flow, the reflected signal traveling through the blood will have a Doppler shift proportional to the velocity of the blood that it is encountering. When there is no blood flow as for example where there is a chronic total occlusion, this condition can be readily ascertained by the Doppler shift which is occurring. As hereinafter explained, the guiding sheath 12 of the present invention can be utilized to ascertain when the lesion has been successfully crossed by the guiding sheath 12 by observing the Doppler shift.

The needle cannula 14 as shown in FIG. 2 consists of a flexible elongate tubular member 56 which has proximal and distal extremities 57 and 58 and a bore or lumen 61 extending therethrough from the proximal extremity 57 to the distal extremity 58. The flexible elongate member 56 is provided with a braid or a coil 62 or a combination thereof to provide the desired kink resistance and torquability. A hub 66 is mounted on the proximal extremity 57 and is provided with a hemostasis valve 67 and a saline flush port 68.

The flexible elongate member 56 can have a suitable length as for example 120–150 cm, typically slightly longer than the guiding sheath so that its proximal extremity is still accessible by the human when it is fully deployed. The flexible elongate tubular member 56 has an outside diameter ranging from 0.010" to 0.015" and an inside diameter of 0.0061" to 0.010". A cannula tip 71 is mounted on the distal extremity 58 and has a length ranging from 1-½ to 5 mm and has a bore 72 extending therethrough having an inside diameter of 0.006" to 0.010". The cannula tip 71 can be formed of a suitable material such as stainless steel or a nickel-titanium alloy commonly called Nitinol. In order to provide additional radiopacity for X-ray imaging, the cannula tip 71 can be clad with platinum or plated with gold or other material having high radiopacity. The cannula tip 71 is provided with a very sharp distal extremity 73 which is formed by providing a taper 74 ranging from 20–40° from the central longitudinal axis of the cannula and preferably approximately 30°.

Suitable means is provided for securing the cannula tip 71 to the distal extremity 58 and as shown in FIG. 1 can be provided by forming an annular recess 76 on the cannula tip 71 and having the distal extremity 58 fitted over the same and bonded thereto by a suitable means such as heat fusing. In addition to augment this connection, circumferentially spaced-apart anchoring holes 77 can be provided within the annular recess 76 as shown in FIG. 3. When the anchoring holes 77 are utilized, the flexible elongate member 56 can be heated to cause the plastic to fuse into the anchoring holes 77 to firmly attach the cannula tip 71 to the distal extremity 58 of the needle cannula 54.

As shown in FIG. 4 the cannula 81 can be formed of a nickel-titanium alloy which has been provided with a helical slot 82 extending substantially the entire length of the same up to the beginning of the grind forming a taper 83 and extending to the sharp distal extremity 84. The helical slot 82 imparts additional flexibility to the cannula tip 81 to facilitate maneuvering the needle cannula 54 in the vessel.

Figure 5:
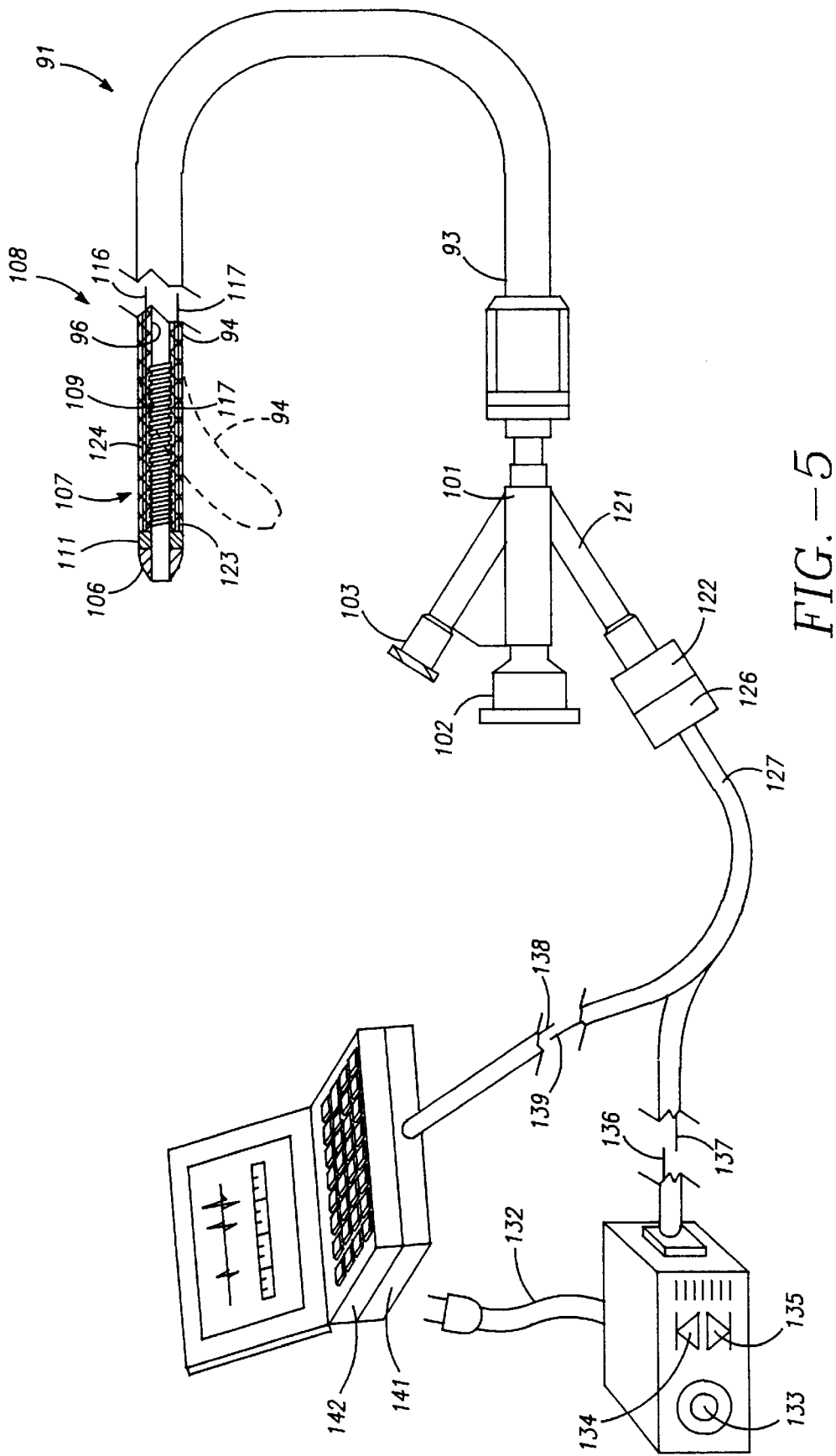
FIG. 5 is a view of another embodiment of a recanalization apparatus incorporating the present invention and showing a side-elevational view partially in section of another embodiment of a guiding sheath.

Another guiding sheath 91 incorporating the present invention is shown in FIG. 5 and consists of a flexible elongate tubular member 92 having proximal and distal extremities 93 and 94 and a lumen 96 extending therethrough from the proximal extremity 93 to the distal extremity 94. The flexible elongate tubular member 92 can have the length and sizes of the type hereinbefore described for the guiding sheath 12. A braid 97 is incorporated therein to provide the desired torquability and kink resistance. A hub 101 is mounted on the proximal extremity 93 and carries a hemostasis value 102 and a saline flush port 103. The distal extremity 94 has a soft tip 106 mounted thereon.

Means in the form of a tip deflection mechanism 107 is provided for deflecting the soft tip 106 to facilitate steering of the guiding sheath 91. This tip deflection mechanism 107 consists of a helical coil 108 wound from a flat ribbon 109 having a cross-sectional area which has a width of 0.010" to 0.015" and a thickness of 0.002" to 0.003". The ribbon 109 is preferably formed of nickel-titanium alloy commonly called Nitinol. The flat ribbon 109 is wound into a helical coil and is then heat treated or annealed so that it has a shape set in the form of a suitable bend as for example a right angle or approximately 90° bend between the two ends of the Nitinol coil 108. The annealing temperature is selected so that the Nitinol coil remains martensitic at body temperature of 37° C. or 98.6° F. The coil 108 after it has been shape set in a manner well known to those skilled in the art will be generally straight at room and body temperature is embedded in the distal extremity 94 as shown in FIG. 5 so that its distal extremity is immediately adjacent the soft tip 106. During the embedding of the coil 108 within the distal extremity 94 the plastic material forming the distal extremity can be fused about the coil 108 with care being taken so that the fusing temperature is below the annealing temperature for the Nitinol coil 108 so that the coil will not lose the predetermined shape memory which has been provided in the coil. By elevating the temperature of the coil 108 so it is slightly above body temperature, the Nitinol coil can become austenitic and take on the preprogrammed shape to cause the distal extremity 94 to bend as shown in dotted lines in FIG. 5. The amount of bending or deflection of the distal extremity 94 is generally directly proportional to the temperature to which the Nitinol has been raised.

An annular ultrasonic transducer 111 is also provided in the distal extremity 94 in the junction between the coil 108 and the soft tip 106.

Means is provided for supplying heat to the coil 108 and consists of conductive wires 116 and 117 which are connected to opposite ends of the coil 108 and which are embedded in the wall of the flexible elongate tubular member 92 and extend into a cord 121 extending from the hub 102 and into a four wire connector 122. The other two wires of the four wire connector 122 are connected to conductive wires 123 and 124 which are also embedded in the wall of the flexible elongate tubular member 92 and are connected to the ultrasonic transducer 111. The connector 122 is connected to another connector 126 which is connected to a cable 127. The cable 127 is connected to a power supply 131 for supplying electrical energy which can be either AC or DC for heating the coil 108. The power supply 131 is connected to a conventional 110–120 volt 60 cycle or 220 volt 50 cycle AC power by a power cord 132. The power supply is provided with conventional controls as for example an on-off switch 133 and increase and decrease pushbuttons 134 and 135 to adjust the application of power to the coil 108. In this way it is possible to achieve the desired amount of deflection of the distal extremity 94 as desired by the physician by supplying energy through two conductors 136 and 137 to the cable 127. In order to free up both hands of the physician using the device, it may be desirable to utilize a foot operated switch (not shown) for controlling the deflection of the distal extremity 94. Although the deflection or bending can only occur in one direction in the distal extremity 94, the physician in utilizing the guiding sheath 91 can rotate the proximal extremity to cause the distal extremity to also rotate and thereby cause the tip 106 to face in different directions during the time it is being deflected. Two conductors 138 and 139 in the cable 127 are connected to an ultrasonic power supply and imaging system 141 of the same type as the ultrasonic power supply and imaging system 36 hereinbefore described. It also includes a notebook computer 142 of the same type as notebook computer 37 hereinbefore described.

Figure 6:
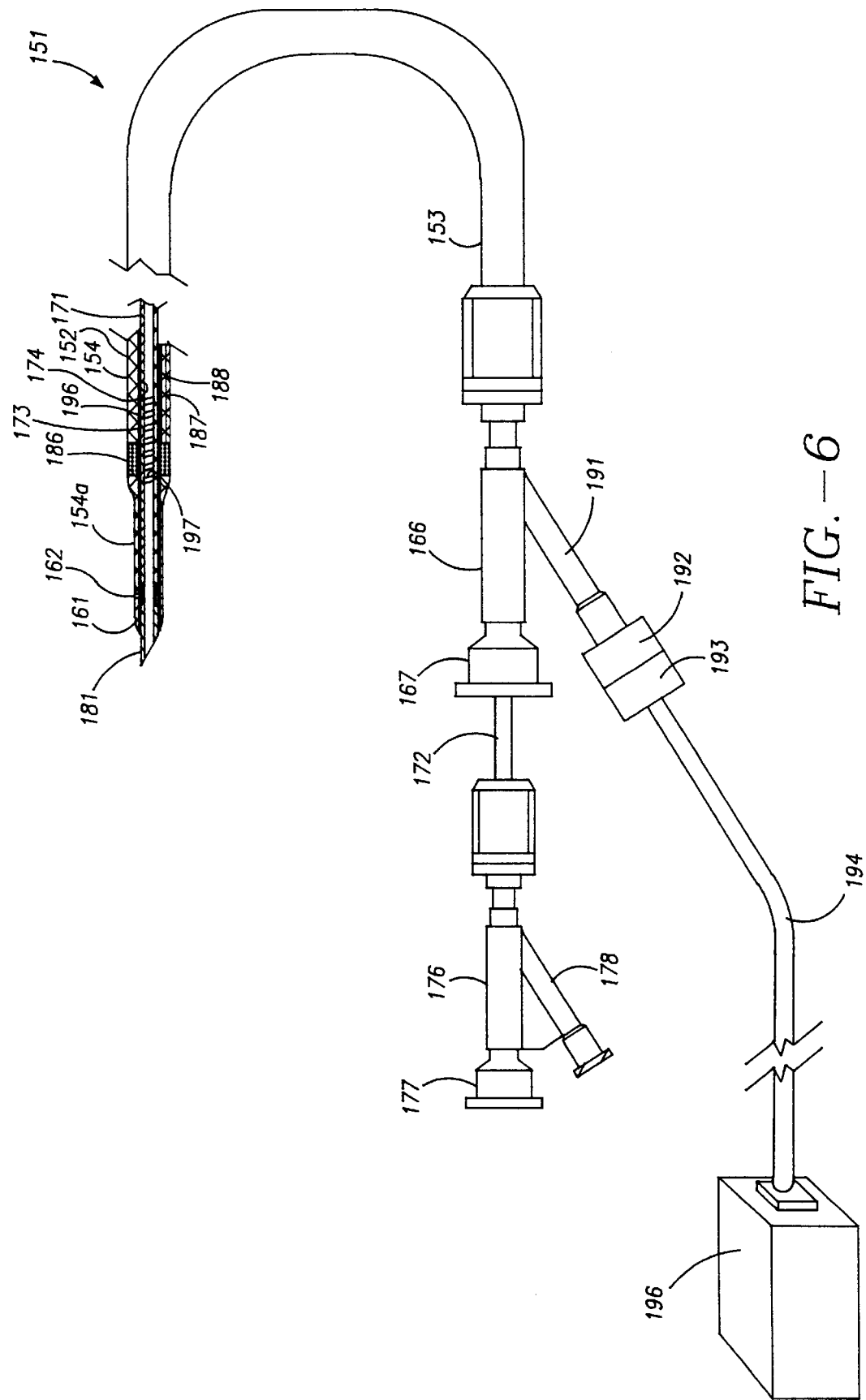
FIG. 6 is a view of still another embodiment of a recanalization apparatus incorporating the present invention and a showing side-elevational view partially in section of another embodiment of a guiding catheter.

Still another guiding sheath 151 incorporating another embodiment of the present invention is shown in FIG. 6 in which there is provided a flexible elongate tubular member 152 having proximal and distal extremities 153 and 154 with a lumen 156 extending therethrough and with a braid 157 embedded within the wall of the tubular member 152. The distalmost portion 154a of the distal extremity 154 has for example a length of approximately 0.5–1.0 cm and is of reduced diameter as for example 0.010" to 0.02" to facilitate crossing a tight lesion. The portion 154a is provided with a soft tip 161 at its distal extremity. An annular ultrasonic transducer 162 of the type hereinbefore described is embedded in the portion 154a just proximal of the soft tip 161.

A hub 166 is mounted on the proximal extremity 153 of the flexible elongate tubular member 152 and carries a hemostasis valve 167. A flexible elongate tubular needle cannula 171 is slidably mounted in the lumen 156 of the flexible elongate tubular member 152 and is provided with proximal and distal extremities 172 and 173 and has a lumen 174 extending therethrough. A hub 176 is mounted on the proximal extremity 172 and carries a hemostasis valve 177. The hub 176 is also provided with a saline flush fitting 178 which is in communication with the lumen 174. The needle cannula 171 is provided with a sharpened tip 181 and is formed of a suitable metal as hereinbefore described and is secured to the distal extremity 173 in a manner hereinbefore described.

Cooperative means is provided on the guiding sheath 151 and on the needle cannula 171 to impart vibratory movement in an axial direction to the tip 181 and consists of a coil 186 formed by an appropriate number of turns of a conductive wire embedded within the distal extremity 154 of the flexible elongate tubular member 152 just proximal of the transition to the portion 154a of reduced diameter. The coil 186 is connected by conductive wires 187 and 188 embedded in the wall of the flexible elongate tubular member 152 and extend through a cord or a cable 191 provided on the hub 166. The cable 191 is connected to a connector 192 which is connected to another connector 193 having a cable 194 connected to an AC power supply 196 that provides variable power at a variable frequency.

The cooperative means includes means provided in the needle cannula 171 in the vicinity of the coil 186 formed of a material having magnetic properties which can be acted upon by variable frequency power supplied to the coil 186. This material having magnetic properties can take many different forms. For example it can be in the form of a highly magnetic material such as a ferrous oxide which is embedded in the plastic of the cannula or alternatively as shown it can take the form of a thin wall tube formed of a silicon iron as for example the tube 196 shown in FIG. 6. If desired, this tube 196 can be provided with helical slots 197 to provide additional flexibility to the distal extremities of the needle cannula 171.

In utilizing the guiding sheath 151 and the needle cannula 171 shown in FIG. 6, the physician, as shown in the cartoon in FIG. 7, advances the guiding sheath 151 until the soft tip 161 is in close proximity to the stenosis or lesion which it is desired to penetrate. The physician can then grasp the proximal extremity 172 of the needle cannula 171 and advance the cannula tip 181 until the physician feels that the cannula tip 181 is in engagement with the lesion forming the total occlusion. Assuming that the physician cannot penetrate the fibrous cap of the lesion with the tip 181, the physician can supply electrical energy from the power supply 196 to cause vibratory movement of the tip 181 in a axial direction while making sure of the direction by the ultrasound imaging system 162 to penetrate the fibrous end cap. In the procedure, the physician can vary the AC frequency over a range by observing instrumentation provided on the power supply 196 and thereby can ascertain where maximum power transfer occurs through the coil 186. The power can then be increased as needed to provide increasing forces in the vibratory motion of the cannula tip 181. This vibratory motion of the tip 181 makes it possible to penetrate even the most fibrous or calcified lesions. During the time this vibratory motion is being applied, the physician can continue to apply gentle pushing forces to the needle cannula until the tip 181 has penetrated the lesion.

Operation and use of the various embodiments of the recanalization apparatus of the present invention may now be briefly described in conjunction with the cartoon shown in FIG. 7. The cartoon shows a vessel 201, such as a coronary artery vessel, having a vessel wall 202 forming a lumen 203 which opens into lumens 204 and 206 in side branches 207 and 208. A total occlusion which may be chronic is formed by a stenosis or lesion 211 in the lumen 203 between the side branches 207 and 208 as shown. The stenosis or lesion, as typical for such total occlusions, has proximal and distal end caps 212 and 213. These end caps 212 and 213 are typically fibrous and difficult to penetrate. The proximal end cap 212 is concave and the distal end cap 213 is convex, as viewed from the left in FIG. 7. Let it be assumed that it is desired to utilize the recanalization apparatus of the present invention in addition in addition to the device which would be used in a conventional PTCA procedure with the exception that it is desired to cross a total occlusion in connection therewith to perform a balloon angioplasty which may or may not be followed by the deployment of a stent. The femoral artery is typically accessed through the groin. Thereafter a conventional guiding catheter 216, not the guiding sheath of the present invention, is deployed through the femoral artery to an orifice of the appropriate coronary artery depicted as vessel 201. A conventional guide wire (not shown), typically a floppy guide wire, is advanced to the total occlusion in question. The conventional guide wire is advanced in the lumen 203 of the vessel 201 so that the distal extremity of the conventional guide wire is in contact with the total occlusion formed by the lesion 211. The guiding sheath 12 or 97 or 151 of the present invention is then advanced over the conventional guide wire into the conventional guiding catheter. As the distal extremity of the guiding sheath is advanced close to the proximal end cap 212, ultrasonic energy is supplied to the ultrasonic transducer carried by the distal extremity to ascertain the position of the tip of the guiding sheath with respect to the wall 202 of the vessel 201 through which it is extending. Using the information obtained from the ultrasonic transducer, the physician advances the guiding sheath until it is in contact with the proximal concave fibrous cap 212 and generally perpendicular to the fibrous cap 212. The needle cannula 54 is then introduced through the bore 22 of the guiding sheath 12 and through the soft tip 19 to the fibrous cap 212. The needle cannula 54 then is pushed through the proximal fibrous cap 212 and through the main body of the lesion 211 and then through the convex distal cap 213. This process can be guided by an ultrasound imaging system in order to be sure that the cannula penetrates through the distal cap into the true lumen. As soon as this has been accomplished, as shown in FIG. 7 a very small conventional guide wire 218, as for example a 0.009" diameter guide wire, is introduced through the lumen 81 in the needle cannula 14 so that it also extends through the lesion. The small guide wire 218 is utilized as a precaution to ensure that the penetration or crossing through the lesion 211 is not lost.

As soon as this has been accomplished, the guiding sheath 12 is advanced through the lesion over the needle cannula 54. The needle cannula 54 with the small guide wire 218 therein is then removed. A conventional guide wire which may be a floppy guide wire (not shown), as for example a 0.014", guide wire, is then advanced through the guiding sheath 12 so that it extends to the other side of and crosses the lesion 211. As soon as this has been accomplished, the guiding sheath 12 of the present invention can be removed with the conventional guide wire left in place. Thereafter, the conventional guide wire can be utilized for directing various devices into the lesion 211 which has been crossed. For example conventional dilatation balloon catheters can be advanced into the lesion to perform a balloon angioplasty. Similarly the same balloon catheter or a different catheter can be utilized for deployment of a stent (not shown) into the lesion which has been crossed and the opening therethrough which has been expanded by the use of balloon angioplasty. Thereafter, all of the devices can be removed and the puncture in the groin closed to complete the procedure.

From the foregoing it can be seen that in the apparatus of the present invention includes a guiding sheath which is capable of being precisely guided so that it extends perpendicular to the lesion which is to be crossed so that when the needle cannula is utilized to penetrate the stenosis, it is assured that the needle extends in a direction perpendicular to the lesion and will not penetrate the vessel wall. In order to further enhance the capabilities of the guiding sheath of the present invention, the distal extremity can be deflected under the control of the physician while at the same time permitting rotation or torquing of the distal extremity so as to ensure that the distal extremity extends in an axial direction which is perpendicular to the fibrous face or fibrous cap of the lesion to ensure that the needle cannula will penetrate the lesion and will not inadvertently penetrate the wall of the vessel in which the lesion is located. More particularly in difficult lesions, vibratory motion can be imparted to the distal extremity of the needle cannula to ensure that penetration of the total occlusion will occur.

What is claimed:

1. A recanalization apparatus for use in crossing a stenosis forming a total occlusion in a lumen in a vessel formed by a vessel wall, the stenosis having a fibrous cap, comprising a guiding sheath comprised of a flexible elongate tubular member having proximal and distal extremities and having a lumen extending from the proximal extremity to the distal extremity, hemostasis valve means mounted on the proximal extremity of the flexible elongate tubular member, a needle cannula slidably mounted in the lumen of the guiding sheath, said needle cannula having proximal and distal extremities and having a lumen extending from the proximal extremity to the distal extremity and a sharpened tip mounted on the distal extremity, said needle cannula having a length so that its proximal extremity extends beyond the proximal extremity of the guiding sheath when the sharpened tip is deployed beyond the distal extremity of the guiding sheath.

2. Apparatus as in claim 1 together with sensing means carried by the distal extremity of the guiding sheath for ascertaining the position of the distal extremity of the guiding sheath with respect to the vessel wall to aid in positioning the distal extremity of the guiding sheath so that it is disposed perpendicular to the fibrous cap of the lesion.

3. Apparatus as in claim 1 wherein said sensing means when carried by the distal extremity of the guiding sheath includes an ultrasonic transducer and means for supplying electrical energy to the transducer and for receiving electrical energy from the transducer.

4. Apparatus as in claim 3 wherein said transducer is in the form of an annulus carried by the distal extremity of the flexible elongate tubular member of the guiding sheath.

5. Apparatus as in claim 1 wherein said needle cannula is provided with a lumen extending from the proximal extremity to the distal extremity and wherein the needle cannula includes a fitting mounted on the proximal extremity for receiving a liquid and for supplying it to the lumen in the needle cannula and a hemostasis valve carried by the proximal extremity.

6. Apparatus as in claim 1 wherein said needle cannula is formed of plastic together with a sharpened metal tip secured to the distal extremity of the needle cannula.

7. Apparatus as in claim 1 wherein said guiding sheath has a braid embedded within the flexible elongate tubular member to reduce kinking of the flexible elongate tubular member and for increasing torque transmission capabilities of the flexible elongate tubular member.

8. Apparatus as in claim 1 wherein said guiding means includes means carried by the distal extremity of the flexible elongate tubular member for deflecting the distal extremity of the flexible elongate tubular member.

9. Apparatus as in claim 8 wherein said means for deflecting the distal extremity of the flexible elongate tubular member of the guiding sheath includes a shape memory element having a shape memory of a predetermined bend therein and means for activating the shape memory element to cause deflection of the distal extremity of the guiding sheath.

10. Apparatus as in claim 9 wherein said shape memory element is formed of a nickel-titanium alloy.

11. Apparatus as in claim 1 wherein said guiding sheath and said needle cannula are provided with cooperative means for supplying vibratory motion to the needle cannula for aid in penetrating the chronic total occlusion.

12. Apparatus as in claim 11 wherein said cooperative means comprises a coil embedded in the guide sheath and magnetic means carried by the needle cannula disposed in the vicinity of the coil and means for supplying variable power at a variable frequency to the coil.

13. A method for crossing a stenosis forming a total occlusion in a lumen in a vessel formed by a vessel wall, the lesion having proximal and distal fibrous caps by the use of a guiding sheath having proximal and distal extremities and having a lumen extending from the proximal extremity to the distal extremity comprising introducing the guiding sheath into the vessel and advancing it in the vessel until the distal extremity is in close proximity to a fibrous cap of the lesion and extends in a direction substantially perpendicular thereto, introducing a needle cannula through the lumen of the guiding sheath and advancing the needle cannula through the fibrous cap and through the lesion and thereafter advancing the guiding sheath over the needle cannula until it penetrates the fibrous cap and the lesion to cross the lesion.

14. A method as in claim 13 wherein the needle cannula includes a lumen extending therethrough, the method further including the steps of advancing a conventional guide wire through the lumen in the needle cannula so it extends through the lesion and thereafter advancing the guiding sheath over the needle cannula and the conventional guide wire.

15. A method as in claim 14 further including the step of removing the needle cannula and the conventional guide wire from the lumen of the guiding sheath and thereafter advancing a larger size conventional guide wire through the guiding sheath and through the total occlusion and thereafter performing additional procedures by advancing devices over the larger size conventional guide wire.

16. A method as in claim 15 wherein the devices advanced over the larger size conventional guide wire are devices to perform balloon angioplasty and stent deployment.

17. A method as in claim 13 wherein the distal extremity of the guiding sheath is guided by the use of ultrasonic energy to ascertain the location of the distal extremity of the guiding sheath with respect to the vessel wall.

18. A method as in claim 13 together with the step of utilizing the ultrasonic energy to ascertain the rate of flow of blood in the vessel and to thereby ascertain when the lesion has been crossed.

19. A method as in claim 13 together with the step of imparting vibratory motion to the needle cannula during the time that the needle cannula is being urged through the fibrous cap and the lesion.

* * * * *